United States Patent
Teramachi

[11] Patent Number: 5,834,304
[45] Date of Patent: Nov. 10, 1998

[54] FERMENTATION TANK

[75] Inventor: Kazuo Teramachi, Nagoya, Japan

[73] Assignee: Toyo Dynam Co. Ltd., Minami-ku, Japan

[21] Appl. No.: 871,618

[22] Filed: Jun. 9, 1997

[51] Int. Cl.[6] .................................................. C12M 3/00
[52] U.S. Cl. ................................. 435/289.1; 435/290.2; 435/291.5; 422/129; 422/225; 422/241
[58] Field of Search ....................... 435/289.1, 290.1, 435/290.2, 291.5; 422/129, 224, 225, 232, 241

[56] References Cited

U.S. PATENT DOCUMENTS

| | | | |
|---|---|---|---|
| 4,090,015 | 5/1978 | Koyanagi et al. | 526/62 |
| 4,169,878 | 10/1979 | Etherington | 422/184 |
| 4,436,818 | 3/1984 | Widmer | 435/316 |
| 5,432,007 | 7/1995 | Naito | 428/447 |
| 5,672,506 | 9/1997 | Aoyagi et al. | 435/289.1 |

*Primary Examiner*—David A. Redding
*Attorney, Agent, or Firm*—Donald S. Dowden, Cooper & Dunham LLP

[57] ABSTRACT

A fermentation tank comprising a tank body wherein an organopolysiloxane film is formed outside and/or inside of said tank body. In said fermentation tank the corrosion of the tank body is prevented, and the penetration of moisture through the tank body into the ground and the penetration of the underground water into the tank body are also prevented.

7 Claims, 3 Drawing Sheets

FERMENTATION TANK

BACKGROUND OF THE INVENTION

1. Field of the Invention

The present invention relates to a fermentation tank. Said fermentation tank may be used to treat mown weed, garbage and the like by the fermentation process to produce feed, food, fertilizer and the like. More particularly, the present invention relates to a fermentation tank comprising a tank body wherein organopolysiloxane film is formed outside and/or inside of said tank body.

2. Description of the Prior Art

FIG. 3 shows an embodiment of a traditional fermentation apparatus (100). As shown in FIG.3, said fermentation apparatus (100) comprises a fermentaiton tank (101) consisting of a tank body (102) providing a stirrer (103) which is driven by a motor (104), sheet heaters (105, 105, 105) attached to the outside of said tank body (102), an exhaust path (107) connected to said tank body (102) and providing a blower (106), and an air inlet path (109) connected to said tank body (102) and providing a valve (108) wherein said tank body (102) has entrances (102A, 102A) of raw material and exits (102B, 102B) of treated material. Stainless steel is mainly used as a material for said tank body (102) to prevent the corrosion or when said fermentaiton tank (101) is installed underground, concrete is also used as a material for said tank body (102).

When raw material such as mown weed, garbage and the like is treated by said fermentation apparatus (100), said raw material M is thrown into said tank body (102) through the entrance (102A, 102A) and further a microorganism is added for fermentation, and then said raw material is stirred and heated in said tank body (102) to ferment aerobically to produce feed, food, fertilizer and the like.

In this fermentation process, gas produced from said raw material in said tank body (102) is exhausted through said exhaust path (107) and the air is supplied to said tank body (102) through said air inlet path (109) by opening said valve (108).

In a case where iron is used as a material for said tank body (102) said tank body (102) will be corroded by the microorganism and in a case where concrete is used as a material for said tank body (102), said tank body (102) will be corroded and further worn.

To solve these problems, as above described, stainless steel is used as a material for said tank body (102). Nevertheless, stainless steel is expensive and has poor processability and further in a case where concrete is used as a material for said tank body (102), besides the problem of corrosion, there is a problem that moisture in said tank body (102) penetrates the concrete wall of said tank body (102) to leak into the ground and mix in the underground water to contaminate the environment around said tank body (102), and conversely, there is also a problem that the underground water penetrates into said tank body (102)

SUMMARY OF THE INVENTION

Accordingly, an object of the present invention is to prevent the corrosion of the tank body of the fermentation tank.

A further object of the present invention is to prevent the penetration of moisture in the tank body of the fermentation tank into the ground.

A still further object of the present invention is to prevent the penetration of the underground water into the tank body of the fermentation tank.

Briefly, said object of the present invention can be attained by a fermentation tank comprising a tank body wherein an organopolysiloxane film is formed outside and/or inside of said tank body.

DETAILED DESCRIPTION OF THE INVENTION

Figure 1:
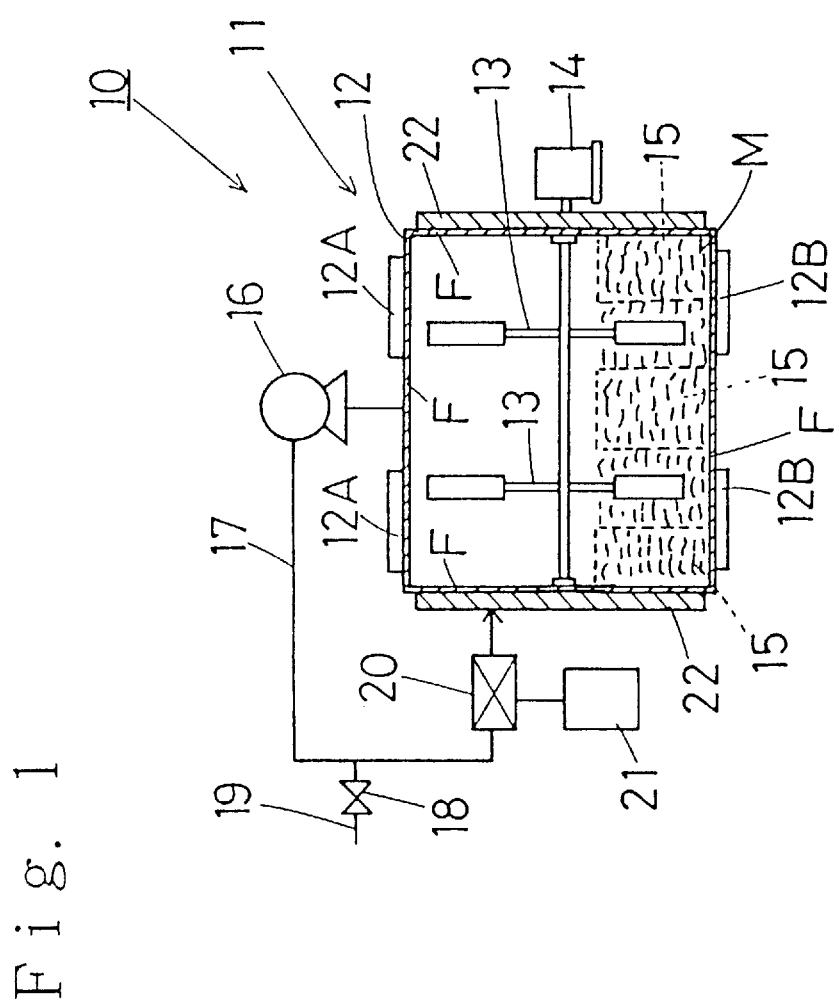
FIG. 1 shows a schematic side sectional view of an embodiment of the present invention.

In the present invention, since the organopolysiloxane film formed outside and/or inside of the tank body consists of polymer having an inorganic main chain consisting of siloxane bonding (—Si—O—), the organopolysiloxane film is superior to general polymer having a main carbon chain in corrosion-resistance, heat-resistance, hardness, surface smoothness and adhesion to inorganic material such as iron, concrete and the like.

In the present invention, to form the organopolysiloxane film outside and/or inside of the tank body, coating material comprising a liquid organopolysiloxane which is dimer, oligomer, prepolymer or low-molecular polymer of organopolysiloxane compound having hydrolytic silyl group such as organochlorosilane, organoalkoxysilane, organoallyloxysilane and the like, and if desirable an additive such as curing catalyst and the like is coated on the outside and/or inside of the tank body and then the resulting film is cured with water if desirable under heating.

The preferable coating material used in the above described coating method is shown in EP Publication No. 0 594 211 A2 and U.S. Pat. No. 5,432,007.

The coating material described in EP Publication No. 0 594 211 A2 is a mixture which contains liquid organosiloxane and hydrated modified organosilicon compound consisting of organosilicon having at least one polyether group and containing therein up to 50% by weight of water wherein said hydrated modified organosilicon compound is contained in said mixture in an amount of at least 30% by weight. If desirable, the coating material may contain one or more cross-linking agent, one or more curing catalyst, one or more filler and the like.

Said organosilicon compound is used to disperse uniformly water into said liquid organosiloxane. The preferable organosilicon compound is silicon oil which is bifunctional type of organopolysiloxane.

As said cross-linking agent, one or more organic compound selected from the group consisting of aluminum compound, boron compound, silicon compound, titanium compound and zirconium compound which has a monovalent organic group and at least one alkoxy group, acyloxy group or oxonium functional group can be used. The typical cross-linking agent is for example methyltrimethoxysilane, phenyltrimethoxysilane, methacryloxypropyltrimethoxysilane, tetrabutoxytitanium, tetrabutoxyzirconium and the like.

As said curing catalyst, organic compound containing metal can be used. The typical curing catalyst is for example alminiumtributoxide, zinc naphtate, dibutylmethinedilaurate, dibutylmethinediacetate and the like.

Said filler can be selected from the group consisting of activating agent which is powdery having particle size of preferably up to 200µ, filler, pigment, colorant and the like. The typical filler is for example titanium oxide, iron oxide (red iron oxide), fine powder of silica, kaolin, zinc borate, carbon black, ultramarine, mica, talc and the like.

The coating material described in U.S. Pat. No. 5,432,007 is solvent-free liquid organopolysiloxane composition which contains said liquid organosiloxane, said crosslinking agent and said curing catalyst.

In the present invention, iron which is easy to process and unexpensive or concrete is mainly used as a material for the tank body of the fermentation tank. Nevertheless since the organopolysiloxane film is formed outside and/or inside of the tank body, in a case where iron is used as a material for the tank body, the tank body is protected from corrosion and in a case where concrete is used as a material for the tank body, the tank body is protected from corrosion and further wear, and moisture in the tank body is checked to penetrate through the concrete wall of the tank body, to leak into the ground and mix in the underground water to contaminate the environment around the fermentation tank, and the underground water does not penetrate the tank body.

FIG. 1 shows an embodiment of a fermentation apparatus of the present invention. As shown in FIG. 1, a fermentation apparatus (10) has a fermentation tank (11) which consists of a tank body (12) providing a stirrer (13). Said tank body (12) has entrances (12A, 12A) of raw material having a lid respectively on the top of said tank body (12) and exits (12B, 12B) of treated material having a lid respectively at the bottom of said tank body (12). Said tank body (12) is made of iron and the organopolysiloxane film F is formed inside of said tank body (12).

Said stirrer (13) is horizontally provided in said tank body (12) and driven by a motor (14). Sheet heaters (15,15,15) are attached to the outside of said tank body (12), and furthermore, a heat insulator (22) is attached around the outside of said tank body (12).

Said fermentation apparatus (10) has a cyclic path (17) connected to said tank body (12). The cyclic path (17) has a blower (16), an air inlet path (19) providing a valve (18), and a condenser (20) connected to a water trap (21).

When raw material M such as mown weed, garbage and the like is treated by said fermentation apparatus (10), said raw material M is thrown into said tank body (12) through the entrance (12A, 12A), by opening the lids and further a microorganism for fermentation is added, and then said lids are closed. Said raw material M is stirred by driving said stirrer (13) and heated in said tank body (12) by said sheet heaters (15, 15, 15) to ferment aerobically to produce feed, food, fertilizer and the like. The heating temperature is generally 60° C. or less.

In this fermentation process, gas produced from said raw material in said tank body (12) is sucked into said cyclic path (17) by said blower (16), and moisture contained in the gas is condensed with the components having bad smell by said condenser (20) and accumlated in said water trap (21). The air is supplied to said tank body (12) through said air inlet path (19) by opening said valve (18).

In this fermentation process, since the organopolysiloxane film is formed inside of said tank body (12), the iron as the material for said tank body (12) is certainly protected from corrosion.

The feed, food, fertilizer and the like obtained by fermenting said raw material M is taken out from said exits (12B, 12B). The condensed water accumlated in said water trap (21) of said condenser (20) is discharged after treatment.

Figure 2:
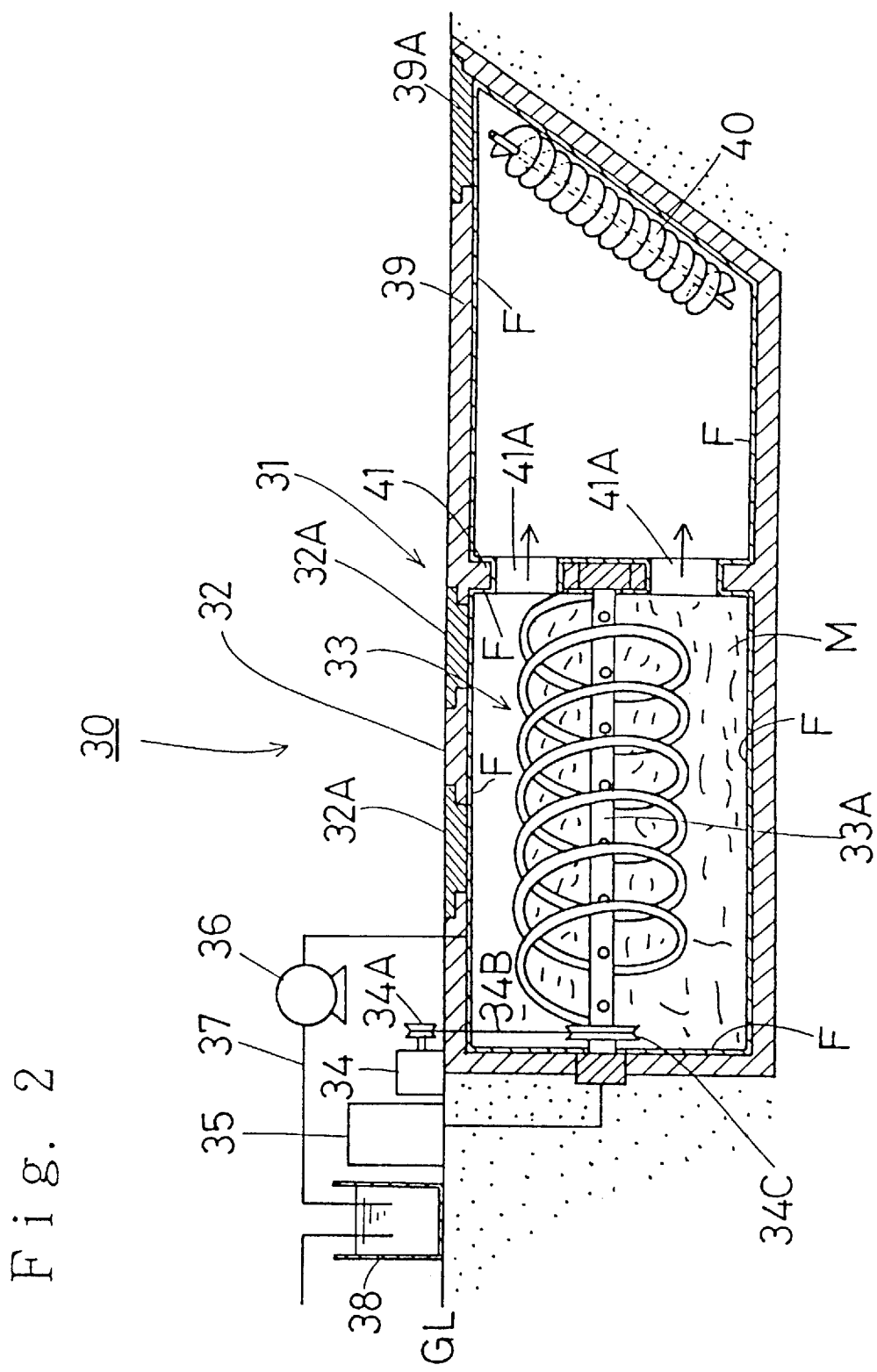
FIG. 2 shows a schematic side sectional view of the other embodiment of the present invention.
Figure 3:
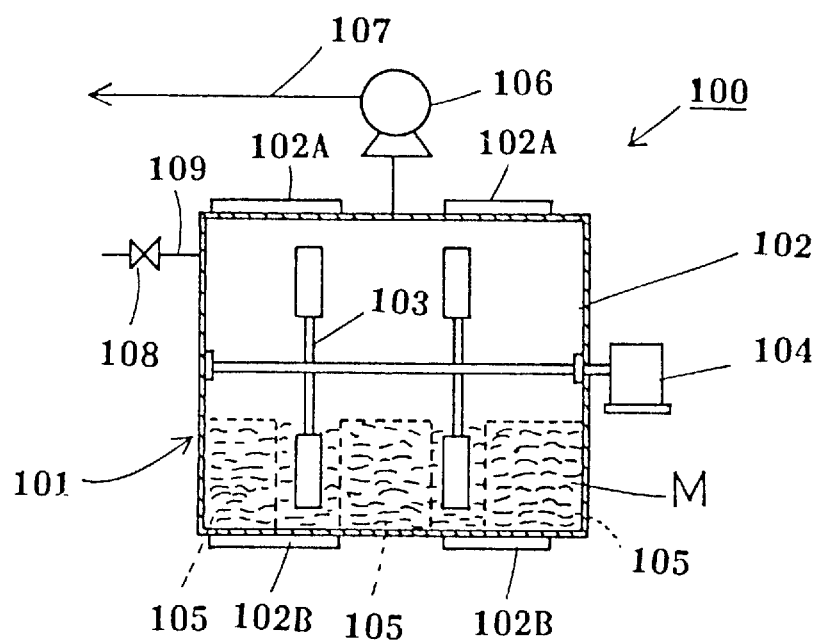
FIG. 3 shows a schematic side sectional view of the traditional fermentation apparatus.

FIG. 2 shows another embodiment of a fermentation apparatus of the present invention. As shown in FIG. 2, a fermentation apparatus (30) comprises a fermentation tank (31) which consists of a tank body (32) providing a screw type stirrer (33). Said fermentation tank (31) is installed underground and provides entrances (32A, 32A) of raw material having a lid respectively at the ground level GL. Said tank body (32) of said fermentation tank (31) is made of concrete and the organopolysiloxane film F is formed inside of said tank body (32). Said screw type stirrer (33) is horizontally provided in said tank body (32). The stirrer (33) is driven by a motor (34) set on the ground GL by intermediating a primary pulley (34A), a belt (34B) and a secondary pulley (34C). The drive shaft (33A) of said stirrer (33) is made of a perforated pipe in which warm air is supplied by a blower (35) set on the ground GL.

An exhaust path (37) is connected to said tank body (32) from the ground GL by intermediating a blower (36) and further a deodorizing tank (38).

A drying tank (39) is installed underground by said fermentation tank (31). Said drying tank (39) may be made of fiber reinforced plastic (FRP), concrete and the like. In a case where concrete is used as a material for the drying tank (39), an organopolysiloxane film F may be formed inside of the drying tank (39). Said drying tank (39) has an exit (39A) having a lid at the ground level GL and a screw conveyor (40) is provided just under said exit (39A) of said drying tank (39). Said drying tank (39) is installed in front of said stirrer (33) of the fermentation tank (31). Between said drying tank (39) and said tank body (32), there is a partition wall (41) having connecting holes (41A,41A).

When raw material M such as mown weed, garbage and the like is treated by said fermentation apparatus (30), said raw material M is thrown into said tank body (32) through the entrance (32A, 32A) by opening the lids and further a microorganism is added for fermentation, and then said lids are closed. Said raw material M is stirred by regular and reverse rotation of said stirrer (33) driven by said motor (34) and is heated by blowing warm air from said blower (35) through said drive shaft (33A) of said stirrer (33). The heating temperature is generally 60° C. or less.

In this fermentation process, said raw material M is stirred in advance and retreat by the regular-reverse in turn rotation of said stirrer (33), as a result said raw material M does not move to said drying tank (39).

Said raw material M is generally fermented for 24 to 72 hours. Gas produced from said raw material in said tank body (32) is sucked into said exhaust path (37) and exhausted after deodorized by said deodorizing tank (38). Said deodorizing tank (38) is filled with activated carbon, water, chlorine dioxide water and the like.

After said fermentation process, fertilizer produced is moved to said drying tank (39) by regular rotation of said stirrer (33) through said connecting holes (41A, 41A) of said partition (41). In said drying tank (39), said fertilizer is dried naturally or heated generally up to 80° C. Dried fertilizer is taken out on the ground by said screw conveyor (40) by opening said lid of the exit (39A).

In this fermentation process, since the organopolysiloxane film is formed inside of said tank body (32), the fermentation tank (31) is certainly protected from corrosion and moisture in the tank body (32) does not penetrate the concrete wall of the tank body (32) to leak into the ground and mix in the underground water to contaminate the environment around the fermentation tank (31), and the underground water does not penetrate into the tank body and prevent fermentation.

In the above described embodiment the organopolysiloxane film F is formed inside of the tank body, but in the present invention the organopolysiloxane film F may be formed inside and outside of the tank body or may be formed only outside of the tank body. Furthermore, the organopolysiloxane film F may be formed not only inside and/or outside of the tank body but also inside and/or outside of the blower, exhaust path and the like.

Since the organopolysiloxane film consists of polymer having inorganic main chain consisting of siloxane bonding (—Si—O—), the organopolysiloxane film has excellent adhesion to the inorganic material such as iron, concrete and the like. As a result, in the fermentation tank of the present invention the corrosion of the tank body and the penetration of the underground water into the tank body can be certainly prevented. Further in the fermentation tank of the present invention, the penetration of moisture in the tank body into the ground can be also prevented and therefore the problem of contaminating the environment around the fermentation tank can be solved.

Furthermore, the inside and/or outside of the tank body is given wear resistance and lubricity by the organopolysiloxane film, as a result the inside and/or outside of the tank body can be protected from damage and abrasion. And the inside and/or outside of the tank body is hard to be stained and if stained, the stained tank body is easily cleaned.

What is claimed is:

1. A fermentation tank comprising:
   a tank body for containing a raw material to be fermented, said tank body being made of a material subject to corrosion by said raw material;
   a stirrer mounted in said tank body; and
   an organopolysiloxane film formed outside and/or inside of said tank body.

2. A fermentation tank according to claim 1 wherein said organopolysiloxane film is formed by coating and curing a coating material consisting of a mixture including liquid organosiloxane and hydrated modified organosilicon compound consisting of organosilicon having at least one polyether group and containing therein up to 50% by weight of water wherein said hydrated modified organosilicon compound is included in said mixture in an amount of at least 30% by weight.

3. A fermentation tank according to claim 1 wherein said organopolysiloxane film is formed by coating and curing coating material consisting of a mixture including a liquid organosiloxane, a cross-linking agent and a curing catalyst.

4. A fermentation tank according to claim 1 wherein iron is used as a material for said tank body.

5. A fermentation tank according to claim 1 wherein concrete is used as a material for said tank body.

6. A fermentation apparatus comprising said fermentation tank according to claim 1.

7. A method comprising the steps of providing a fermentation apparatus according to claim 6 and employing said apparatus to effect fermentation.

* * * * *

UNITED STATES PATENT AND TRADEMARK OFFICE
CERTIFICATE OF CORRECTION

PATENT NO. : 5,834,304
DATED : November 10, 1998
INVENTOR(S) : Kazuo Teramachi

It is certified that error appears in the above-identified patent and that said Letters Patent is hereby corrected as shown below:

On the title page, Foreign Application Priority Data item [30], should be shown as --Application No. 8-171804 filed June 10, 1996, in Japan--

Signed and Sealed this

Eighteenth Day of May, 1999

Attest:

Q. TODD DICKINSON

Attesting Officer

Acting Commissioner of Patents and Trademarks